(12) United States Patent
Li

(10) Patent No.: US 7,125,868 B2
(45) Date of Patent: Oct. 24, 2006

(54) THIENOTHIAZINE COMPOUND HAVING ANTI-INFLAMMATORY AND ANALGESIC PROPERTIES AND METHOD OF MAKING AND USING THE SAME

(76) Inventor: Jing Li, Suite 410, The building of Scientific Incubator of Oversea Students Shangdi Dong Lu 29 Hao, Haidian District, Beijing 100085 (CN)

( * ) Notice: Subject to any disclaimer, the term of this patent is extended or adjusted under 35 U.S.C. 154(b) by 0 days.

(21) Appl. No.: 10/746,415

(22) Filed: Dec. 24, 2003

(65) Prior Publication Data

US 2004/0157835 A1    Aug. 12, 2004

Related U.S. Application Data

(63) Continuation-in-part of application No. PCT/CN02/00437, filed on Jun. 24, 2002.

(30) Foreign Application Priority Data

Jun. 25, 2001  (CN) ............................... 01 1 18886

(51) Int. Cl.
C07D 513/04    (2006.01)
A61K 31/542    (2006.01)
(52) U.S. Cl. ..................... 514/226.5; 544/48
(58) Field of Classification Search ............... 544/48; 514/226.5
See application file for complete search history.

(56) References Cited

U.S. PATENT DOCUMENTS 4,076,709 A    2/1978    Hromatka et al.
4,180,662 A    12/1979   Pfister et al.
5,679,678 A *  10/1997   Binder et al. ............. 514/226.5

FOREIGN PATENT DOCUMENTS

| CH | 1519811 | 8/1978 |
| CN | 1083066 | 3/1994 |
| CN | 1109059 | 9/1995 |
| CN | 011188863 | 6/2001 |

OTHER PUBLICATIONS

Nishimoto et al. Current Opinion in Pharmacology 2004, 4:386-391.*

* cited by examiner

Primary Examiner—Kahsay Habte
(74) Attorney, Agent, or Firm—Yi Li

(57) ABSTRACT

The present invention is related to a type of thienothiazine compounds having molecular structure of formula (1) and their pharmaceutically acceptable salts or solvates. The present invention is also related to the method of producing the formula (1) compound, an anti-inflammatory and analgesic pharmaceutical composition containing the formula (1) compound, and the method of using the formula (1) compound to prepare anti-inflammatory and analgesic medicine

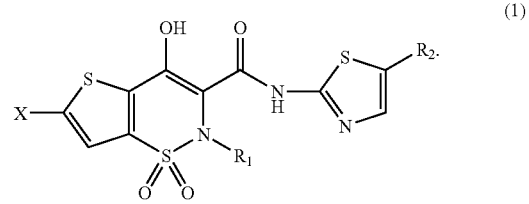

(1)

10 Claims, 1 Drawing Sheet

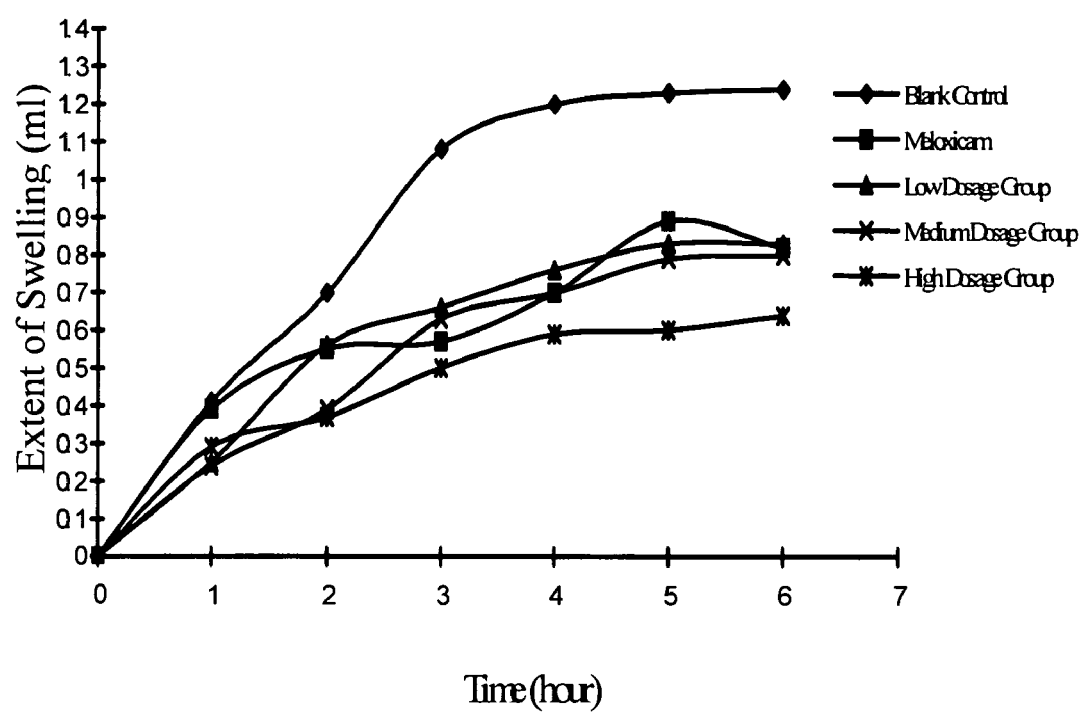
Fig. 1  Effect on Carrageenan Induced Rat Foot Swelling Model

THIENOTHIAZINE COMPOUND HAVING ANTI-INFLAMMATORY AND ANALGESIC PROPERTIES AND METHOD OF MAKING AND USING THE SAME

CROSS REFERENCE TO RELATED APPLICATION

This application is a Continuation-In-Part and claims priority of PCT patent application Ser. No. PCT/CN02/00437 filed Jun. 24, 2002, which claims the priority of Chinese patent application No. 01118886.3 filed Jun. 25, 2001, which are hereby incorporated by reference in its entirety.

FIELD OF THE INVENTION

The present invention is related to organic chemistry and pharmaceutical chemistry. More specifically, the present invention is related to thienothiazine compounds which have anti-inflammatory and analgesic properties, and this compound is characterized by the selective inhibition of cyclooxygenase-2, anti-inflammatory and analgesic properties, and no side effects of causing ulcer with the treatment dosage.

BACKGROUND OF THE INVENTION

As early as in 1971, Vane and his colleagues discovered that aspirin type nonsteroidal anti-inflammatory drug (NASID) have anti-inflammatory, analgesic and antifebrile functions by inhibiting Cyclooxygenase (CoX) and blocking prostaglandin synthesis from arachidonic acid. Vane et al also pointed out that the side effects caused by NSAID, such as irritation to stomach and intestines, and damages to kidney are also due to the elimination of the physiological prostaglandin which can protect stomach and kidney. Vane et al's views have been commonly accepted.

In the past twenty years, various researches have focused on the improvement of therapeutic effects of the NSAID and the reduction of the corresponding side effects through many methods, particularly on the improvement on the dosage forms of the medicines. For example, the medicines have been made into suppository, enteric-coated form and time-release form. There are also a substantial progress in the development of pharmaceuticals based on new chemicals and the development of the precursors.

In 1991, Herschman and Simmono using molecular cloning confirmed the second isoenzyme, named Cyclooxygenase-2 (CoX-2). Many subsequent literatures have demonstrated that CoX-2 is expressed in the inflammatory tissue and is controlled by glucocorticoid (GG). It is believed that CoX-2 can be the target of NSAID, which may provide a reasonable explanation for the side effects resulting from the inhibition of the CoX-1. Therefore, the discovery of CoX-2 has led the new trend of developing selective CoX-2 inhibitors.

It has been observed that many NSAID have a strong inhibiting effect on CoX-1 and a weak inhibiting effect on CoX-2. In other words, almost all the previously discovered NSAID can inhibit CoX-1. Furthermore, the stronger the inhibiting effect of a medicine has on CoX-1, the more side effects it has. While the stronger the inhibiting effect of a medicine exerts on CoX-2, the more effective the medicine is therapeutically. At present the ratio of CoX-1/Cox-2 is commonly used to express the effectiveness of inhibition of CoX-1 and CoX-2 by NSAID. The higher the ratio is, the stronger the inhibition of CoX-1 and in turn more side effects are. On the contrary, the lower the ratio is, the less the side effects.

At present, commercially available selective CoX-2 inhibitors are as follows:

(1) Meloxicam

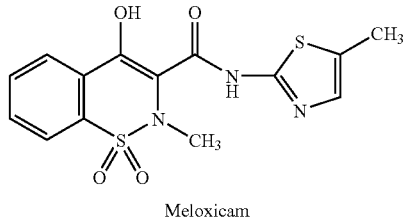

Meloxicam

This medicine is commercially available in many countries, and has been used to treat thousands of patients clinically. It is the representative of this type of medicine for treating osteoarthritis and rheumatic arthritis. (2) Celecoxib demonstrates the selective inhibition of CoX-2 by the animal arthritis and pain model. It also proves effectiveness in the similar treatment of human. The existing experimental results have demonstrated that in comparison with the previous NSAID, Celecoxib has an equavelent or better therapeutic effects and less side effects. (3) Vioxx has already been used clinically in the North America to treat osteoarthritis and release pain from tooth extraction. (4) Minesulide has already been used clinically in the United States and Europe.

SUMMARY OF THE INVENTION

One objective of the present invention is to provide a highly effective anti-inflammatory and analgesic compound. More specifically, the present invention provides thienothiazine compounds having molecular structure (1) and the pharmaceutically acceptable salts or solvates thereof:

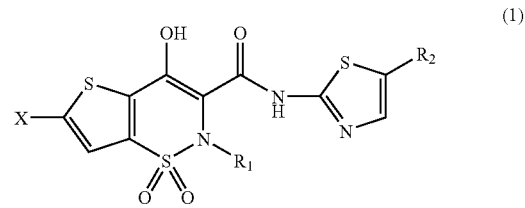

wherein $R_1$ is $C_{1-4}$ alkyl, including methyl, ethyl, propyl, isopropyl and butyl; $R_2$ is $C_{1-4}$ alkyl, including methyl, ethyl, propyl, isopropyl and butyl; X is F, Cl, Br, $OCH_3$ and OH. This compound has anti-inflammatory and analgesic properties of the nonsteroidal anti-inflammatory drug, and very low side effects in term of causing ulcer, and it has the characteristics of CoX-2 inhibitor, and is a very promising anti-inflammatory and analgesic medicine.

A further objective of the present invention is to provide a method of producing formula (1) compound. The method includes the reaction between the following formula (2) compound and formula (3) compound. With regard to the production of formula (2) compound, please refer to the U.S. Pat. No. 4,180,662A. The method of making formula (2) compound is described in U.S. Pat. No. 4,180,662A, which is hereby incorporated by reference in its entirety. Formula (3) compound is a chemical which can be purchased commercially.

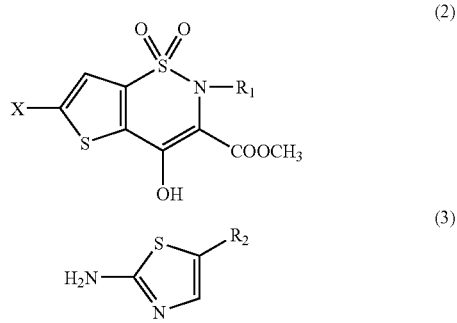

wherein $R_1$, $R_2$ and X are as defined above in formula (1).

Another objective of the present invention is to provide a pharmaceutical composition containing the formula (1) compound as the active component and pharmaceutically acceptable auxiliary or carriers.

Yet another objective of the present invention is to provide a method of making anti-inflammatory and analgesic medicines using the formula (1) compound.

DESCRIPTION OF THE INVENTION

The procedure of synthesizing the formula (1) compound is as follows: add formula (2) compound, formula (3) compound and anhydro-dimethylbenzene into a dry flask, mix with heating until reflux; reflux for a certain period of time, and then introduce nitrogen gas to remove methanol resulted from the reaction; continue reflux for several hours, then cool down, and put the reaction mixture in the refrigerator to crystallize the solid; filter the solid by vacuum; wash the solid with an appropriate amount of organic solvent; let the solid dry to obtain the formula (1) compound.

The formula (1) compounds have important bioactivities. The pharmacodynamic experiments have shown that the formula (1) compound has substantial effects in inhibiting dimethylbenzene induced mouse ear swelling, chemical stimulus induced pain, and carrageenan induced rat foot swelling. Furthermore, the experiments have shown evident relationship between the dosage and effectiveness. These compounds can inhibit induced primary and secondary inflammations of rats on a dosage dependent basis. In comparison to the representative medicine of the same class, Meloxicam, the formula (1) compounds have less side effects in causing rat stomach ulcer. The formula (1) compounds have enhanced therapeutic effect and reduced side effects. The LD 50 (the single dosage causing 50% death of the testing animals) by oral and abdominal administration is in the range of from 200 to 500 mg/kg.

The formula (1) compounds or their pharmaceutically acceptable salts or solvates can be combined with commonly used auxiliary or carriers to produce anti-inflammatory and analgesic pharmaceutical composition. This pharmaceutical composition can be in the form of injection solution, tablet or capsule.

BRIEF DESCRIPTION OF DRAWINGS

FIG. 1 is the obtained curve showing the effect on the carrageenan induced rat foot swelling model, wherein the abscissa indicates time (hour), and the y-axis indicates the extent of the swelling.

DETAILED EMBODIMENTS

The present invention is further described in detail with following examples.

EXAMPLE 1

Synthesis of 6-chlorine-4-hydroxy-2-methyl-N-[2'-(5'-methyl)thiazolyl]-2H-thieno-[2,3-e]-1,2-thiazine-3-formamide-1,1-dioxide

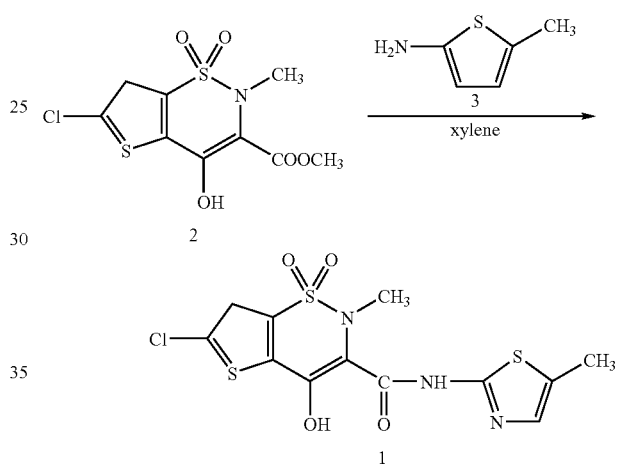

Add the compound (2) (1.5 g, 0.005 mol), 2-amido-5-methyl thiazole (compound 3) (0.75 g, 0.0065 mol) and dimethylbenzene (180 mL) into a 500 mL dry tri-neck round bottom flask; reflux with mixing under nitrogen atmosphere for ten hours, then cool down the reaction mixture; filter to obtain 1.2 g yellow crystal of 6-chlorine-4-hydroxy-2-methyl-N-[2'-(5'-methyl) thiazolyl]-2H-thieno-[2,3-e]-1, 2-thiazine-3-formamide-1,1-dioxide, m.p.: 245~250° C.; MS(m/z): 392, 374, 328, 141, 115; $^1$HNMR (DMSO-$d_6$): δ 2.328 (d, 3H, J=6), 2.937 (s, 3H), 7.364 (s, 1H, J=6), 7.678 (s, 1H); $^{13}$CNMR(DMSO-$d_6$): 165.528, 163.503, 155.943, 138.012, 136.395, 134.720, 124.305, 122.572, 111.559, 38.320, 11.664.

EXAMPLE 2

Experiment of the Mouse Ear Swelling

Divide the mice randomly into five groups, with each team consisting of ten mice. The five groups are respectively the blank control group, the positive medicine control (Meloxicam) group, and the testing groups which use low, medium and high dosages of the compound of Example 1. The mice of the positive medicine group were fed orally with 8 mg/kg Meloxicam, and the mice of the three testing groups were fed with 2 mg/kg (low), 4 mg/kg (medium) and 8 mg/kg (high), respectively, the compound synthesized in Example 1. Dimethylbenzene was used to induce ear swelling of the mice. The inhibition rate of the positive medicine group was 43%, and the inhibition rate of the low, medium and high dosage testing groups were 56%, 67% and 81%, respectively, which were significantly different from the blank control group (p<0.01), as shown in Table 1.

EXAMPLE 3

Rat Inflammation Test

Divide the rats randomly into five groups, with each group consisting of ten rats. The five groups are the blank control group, the positive medicine control group (Meloxicam 4 mg/kg), and the testing groups which use low, medium and high dosages of the compound of Example 1. Use carrageenan induced inflammation to cause rat plantar swelling. The rats of the testing groups took 1 mg/kg (low), 2 mg/kg (medium) and 4 mg/kg (high), respectively, of the compound synthesized in Example 1. 2–6 hours after induced inflammation, the plantar swelling rate of the testing groups was significantly different from that of the blank control group (p<0.01–0.001). Furthermore, the compound (1) is substantially more effective than the positive medicine Meloxicam (see Table 2 and FIG. 1).

EXAMPLE 4

Effects on the Pain Caused by Chemical Stimuli

The mice in testing groups were orally fed with 2 mg/kg, 4 mg/kg and 8 mg/kg of the compound synthesized in Example 1. The chemical stimuli induced pain (acetic acid body twist reaction) of the mice in the testing groups were significantly different from that of the blank control group (p<0.01–0.001). The percentage of body twist for the 2 mg/kg (low), 4 mg/kg (medium) and 8 mg/kg (high) groups were 90%, 80% and 60%. In comparison to the percentage of body twist (100%) of the positive medicine Meloxicam (8 mg/kg), the compound synthesized in Example 1 was substantially more effective (see Table 3).

EXAMPLE 5

Effects on Inflammation Induced by Adjuvant

The rats in the testing groups orally took 1 mg/kg (low), 2 mg/kg (medium) and 4 mg/kg (high) of the compound synthesized in Example 1, and showed dosage dependent inhibition of the primary and secondary inflammation induced by adjuvant. The compound synthesized in Example 1 showed substantial inhibition of the rat foot swelling at eighteen hours, twenty fourth hours, third days, eighth days and nineteen days after inflammation being induced, which was significantly different from the blank control group, P<0.01. The compound synthesized in Example 1 was substantially more effective in comparison to Meloxicam (see Table 4).

EXAMPLE 6

Examination of the Side Effects of Causing Ulcer

It was observed that among the rats which took orally 1 mg/kg (low), 2 mg/kg (medium) and 4 mg/kg (high) the compound synthesized in Example 1 continuously for four successive days, the occurring rate of ulcer increased with increased dosage, with corresponding ulcer occurring rate of 0%, 30% and 80%, respectively. In comparison with 4 mg/kg Meloxicam, which had the ulcer occurring rate of 100%, the compound synthesized in Example 1 had less side effect (P<0.01, see Table 5).

EXAMPLE 7

Preparation of Injection Solution

Select the compound synthesized in Example 1, which meet pharmaceutical preparation standard, as the raw material, and sieve the raw material. Mix 8 weight units of the compound of Example 1, 100 weight units of mannitol and 40 weight units of PEG-400 homogeneously; add injection use water and mix; then add 1 mol/L NaOH solution with mixing until pH was 9.45. Add active carbon, mix for twenty minutes at room temperature, then separate the active carbon. Then add injection use water to obtain a final concentration of the compound synthesized in Example 1 of about 4 mg/ml, and mix it homogeneously. Filter with 0.22 μm micropore membrane in accordance with the aseptic operation in a class 100 laminar flow super-clean room. Upon passing the qualification examination, fill the composition into 6 ml brown sealing bottles under aseptic condition and insert venting rubber stopper. Put the bottles in a lypholyser, freeze, after three hours apply vacuum; sublimation-drying for 24 hours, then seal and cover the stopper with the aluminum cover. Package the sealing bottles after quality assurance check. Every sealing bottle contained 8 mg the compound of Example 1.

TABLE 1

Effect upon Dimethylbenzene Induced Mouse Ear Swelling

| Group | Dosage (mg/kg) | Rate of Ear Swelling ($\bar{x} \pm s$) |
|---|---|---|
| Blank control group | — | 1.12 ± 0.30 |
| Meloxicam | 8 | 0.43 ± 0.36** |
| Low | 2 | 0.56 ± 0.35** |
| Medium | 4 | 0.67 ± 0.43** |
| High | 8 | 0.81 ± 0.26** |

Note:
in comparison with the blank control group
**P < 0.01.

TABLE 2

Effects upon the Carrageenan Induced Rat Foot Swelling (n = 10, $\bar{x} \pm S$)

| Group | Dosage (mg/kg) | Change in the Foot Volume at Certain Hours after Giving the Carrageenan | | | | | |
|---|---|---|---|---|---|---|---|
| | | One hour | Two hours | Three hours | Four hours | Five hours | Six hours |
| Blank Control Group | — | 0.41 ± 0.18 | 0.70 ± 0.20 | 1.08 ± 0.21 | 1.20 ± 0.24 | 1.23 ± 0.24 | 1.24 ± 0.29 |
| Meloxicam | 4.0 | 0.39 ± 0.15 | 0.55 ± 0.21 | 0.57 ± 0.33** | 0.70 ± 0.34** | 0.89 ± 0.33* | 0.82 ± 0.39* |
| Low | 1.0 | 0.25 ± 0.15 | 0.56 ± 0.27 | 0.66 ± 0.34** | 0.76 ± 0.28** | 0.83 ± 0.28** | 0.83 ± 0.25** |
| Medium | 2.0 | 0.24 ± 0.11* | 0.39 ± 0.17** | 0.63 ± 0.54** | 0.70 ± 0.25*** | 0.79 ± 0.25** | 0.80 ± 0.21** |
| High | 4.0 | 0.29 ± 0.20 | 0.37 ± 0.22** | 0.50 ± 0.20*** | 0.59 ± 0.30*** | 0.60 ± 0.31*** | 0.64 ± 0.24** |

Note:
in comparison with the same time blank control group
*$p < 0.05$,
**$p < 0.01$,
***$p < 0.001$

TABLE 3

Analgesic Effects upon the Body Twist Reaction Induced by Acetic Acid

| Group | Dosage (mg/kg) | Numbers of Occurrence of Body Twist ($\bar{x} \pm s$) | Percentage of Body Twist (%) |
|---|---|---|---|
| Blank Control Group | — | 44.22 ± 21.200 | 100 |
| Meloxicam | 8.0 | 18.11 ± 14.37** | 100 |
| High | 8.0 | 2.78 ± 3.49*** | 60 |
| Medium | 4.0 | 10.78 ± 8.15** | 80 |
| Low | 2.0 | 14.78 ± 6.38** | 90 |

Note:
in comparison with the blank control group
**$P < 0.01$,
***$P < 0.001$

TABLE 4

Effects upon the Adjuvant Induced Rat Foot Swelling ($\bar{x} \pm S$, n = 10)

| Group | Dosage (mg/kg) | Rate of the Change in the Volume of Left and Right Feet at Certain Time after Giving Adjuvant | | | | |
|---|---|---|---|---|---|---|
| | | 18 hours | 24 hours | 3 days | 8 days | 19 days |
| Blank Control Group | — | 0.86 ± 0.17 | 0.96 ± 0.10 | 1.00 ± 0.13 | 1.12 ± 0.09 | 1.10 ± 0.12 |
| Meloxicam | 4.0 | 0.78 ± 0.13 | 0.76 ± 0.20* | 0.75 ± 0.14** | 0.76 ± 0.23*** | 0.99 ± 1.29 |
| Low | 1.0 | 0.77 ± 0.28 | 0.75 ± 0.24** | 0.74 ± 0.28** | 0.75 ± 0.29** | 0.97 ± 0.19 |
| Medium | 2.0 | 0.62 ± 0.10** | 0.60 ± 0.10*** | 0.61 ± 0.13** | 0.60 ± 0.14*** | 0.69 ± 1.10 |
| High | 4.0 | 0.65 ± 0.08** | 0.65 ± 0.12** | 0.53 ± 0.13*** | 0.63 ± 0.16*** | 0.72 ± 1.12 |

Note:
in comparison with the same time blank control group
*$P < 0.05$,
**$P < 0.01$,
***$P < 0.001$

TABLE 5

Effects on Causing Rat Gastric Mucosa Ulcer

| Group | Dosage (mg/kg) | Number of the animals (unit) | Ulcer Occurring Rate (%) |
|---|---|---|---|
| Blank Control Group | — | 10 | 0 |
| Meloxicam | 4 | 10 | 100 |
| High | 4 | 10 | 80 |
| Medium | 2 | 10 | 30 |
| Low | 1 | 10 | 0 |

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A thieno-[2,3-e]-1,2-thiazine compound having a structure of formula (1) and pharmaceutical acceptable salts or solvates thereof:

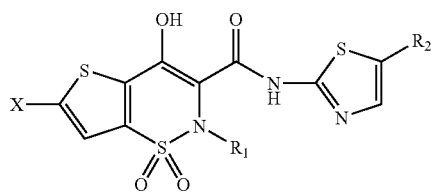

(1)

wherein $R_1$ is methyl, ethyl, propyl, isopropyl or butyl; $R_2$ is methyl, ethyl, propyl, isopropyl or butyl; and X is F, Cl, Br, OCH$_3$ or OH.

2. The compound according to claim 1, wherein said compound is 6-chlorine-4-hydroxy-2-methyl-N-[2'-(5'-methyl) thiazolyl]-2H-thieno-[2,3-e]-1, 2-thiazine-3-formamide -1,1-dioxide.

3. A method of producing a formula (1) compound comprising reacting a formula (2) compound with a formula (3) compound,

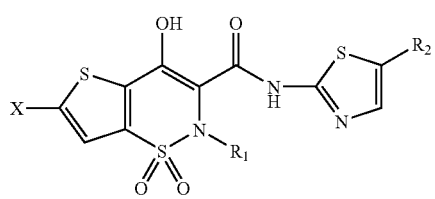

(1)

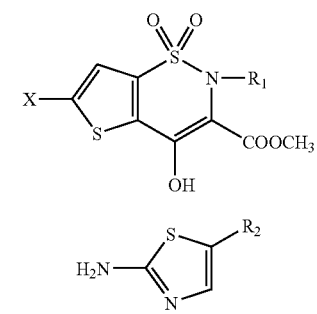

wherein $R_1$ is methyl, ethyl, propyl, isopropyl or butyl; $R_2$ is methyl, ethyl, propyl, isopropyl or butyl; and X is F, Cl, Br. OCH$_3$ or OH.

4. The method according to claim 3, wherein said formula (1) compound is 6-chlorine-4-hydroxy-2-methyl-N-[2'-(5'-methyl) thiazolyl]-2H-thieno-[2,3-e]-1,2-thiazine-3-formamide -1,1-dioxide.

5. A pharmaceutical composition comprising:
(a) a formula (1) compound as active component,

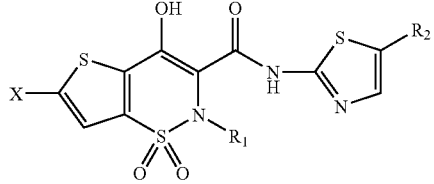

(1)

wherein $R_1$ is methyl, ethyl, propyl, isopropyl or butyl; $R_2$ is methyl, ethyl, propyl, isopropyl or butyl; and X is F, Cl, Br, OCH$_3$ or OH; and (b) a pharmaceutical auxiliary or carrier.

6. The pharmaceutical composition according to claim 5, wherein said formula (1) compound is 6-chlorine-4-hydroxy-2-methyl-N-[2'-(5'-methyl) thiazolyl]-2H-thieno-[2, 3-e]-1,2-thiazine-3-formamide -1,1-dioxide.

7. The pharmaceutical composition according to claim 5, wherein said pharmaceutical composition is in a form of tablet, capsule or injection solution.

8. The pharmaceutical composition according to claim 6, wherein said pharmaceutical composition is in a form of tablet, capsule or injection solution.

9. A method of making an anti-inflammatory and analgesic medicine comprising:
(a) providing a compound defined by formula (1), (1)

wherein $R_1$ is methyl, ethyl, propyl, isopropyl or butyl; $R_2$ is methyl, ethyl, propyl, isopropyl or butyl; and X is F, Cl, Br, OCH$_3$ or and (b) mixing said compound with a pharmaceutical auxiliary or carrier to produce said medicine.

10. A method according to claim 9, wherein the formula (1) compound is 6-chlorine-4-hydroxy-2-methyl-N-[2'-(5'-methyl) thiazolyl]-2H-thieno-[2,3-e]-1,2-thiazine-3-formamide -1,1-dioxide.

* * * * *